United States Patent
Mertler et al.

(10) Patent No.: US 8,181,505 B2
(45) Date of Patent: May 22, 2012

(54) MEASUREMENT SYSTEM FOR THE MULTIDIMENSIONAL AEROSOL CHARACTERIZATION

(75) Inventors: Michael Mertler, Freinsheim (DE); Bernd Sachweh, Meckenheim (DE); Markus Linsenbühler, Ludwigshafen (DE); Michael Schäfer, Altrip (DE); David Y. H. Pui, Plymouth, MN (US); Heinz Fissan, Kerken (DE); Jing Wang, Minneapolis, MN (US); Weon Gyu Shin, Falcon Heights, MN (US)

(73) Assignees: BASF SE, Ludwigshafen (DE); Regents of The University of Minnesota, South Minneapolis, MN (US)

( * ) Notice: Subject to any disclaimer, the term of this patent is extended or adjusted under 35 U.S.C. 154(b) by 602 days.

(21) Appl. No.: 12/366,963

(22) Filed: Feb. 6, 2009

(65) Prior Publication Data
US 2009/0199623 A1 Aug. 13, 2009

Related U.S. Application Data

(60) Provisional application No. 61/026,592, filed on Feb. 6, 2008.

(51) Int. Cl.
*G01N 27/60* (2006.01)
(52) U.S. Cl. .......... 73/31.03; 73/31.01; 73/31.02; 250/281; 250/283; 702/29
(58) Field of Classification Search .......... 73/31.01, 73/31.02, 31.03, 31.07; 250/281, 282, 294, 250/297, 301; 702/29
See application file for complete search history.

(56) References Cited

U.S. PATENT DOCUMENTS

| | | | |
|---|---|---|---|
| 4,790,650 A | 12/1988 | Keady | |
| 5,596,136 A * | 1/1997 | Flagan et al. | 73/28.04 |
| 5,973,904 A | 10/1999 | Pui et al. | |

(Continued)

FOREIGN PATENT DOCUMENTS

DE 198 46 656 A1 4/1999

(Continued)

OTHER PUBLICATIONS

Anshuman Amit Lall, et al., "On-Line Measurement of Ultrafine Aggregate Surface Area and Volume Distributions by Electrical Mobility Analysis: I. Theoretical Analysis", Aerosol Science, vol. 37, 2006, pp. 260-271.

(Continued)

*Primary Examiner* — David Rogers
(74) *Attorney, Agent, or Firm* — Oblon, Spivak, McClelland, Maier & Neustadt, L.L.P.

(57) ABSTRACT

A method is proposed for characterizing a totality of particles. The method can be used in particular for characterizing microparticular or nanoparticular aerosols. The method comprises the following steps:
a) in a classification step, a class of the totality is selected, wherein the particles of the selected class have a pre-specified mobility $d_m$;
b) in a counting step, a number N of the particles of the selected class is determined;
c) in a charge determination step, a charge Q of the particles of the selected class is determined; and
d) in an evaluation step, at least one morphological parameter is determined from the charge Q, the number N and the mobility $d_m$, wherein the morphological parameter comprises at least one item of information about an agglomerate state of the particles.

42 Claims, 7 Drawing Sheets

U.S. PATENT DOCUMENTS

| | | | |
|---|---|---|---|
| 6,051,189 A * | 4/2000 | Wick et al. | 422/82.01 |
| 6,145,391 A | 11/2000 | Pui et al. | |
| 6,386,015 B1 * | 5/2002 | Rader et al. | 73/31.05 |
| 6,567,157 B1 * | 5/2003 | Flagan et al. | 356/37 |
| 7,105,042 B2 | 9/2006 | Tumbrink et al. | |
| 7,222,517 B2 * | 5/2007 | Schiefer | 73/28.01 |
| 7,250,138 B2 * | 7/2007 | Wick | 422/50 |
| 7,470,898 B2 * | 12/2008 | Merrick et al. | 250/286 |
| 7,485,854 B2 * | 2/2009 | Hartonen et al. | 250/288 |
| 7,518,108 B2 * | 4/2009 | Frey et al. | 250/288 |
| 2004/0080321 A1 | 4/2004 | Reavell et al. | |
| 2005/0045818 A1 * | 3/2005 | De La Mora et al. | 250/294 |
| 2006/0150754 A1 | 7/2006 | Burtscher et al. | |
| 2006/0266132 A1 | 11/2006 | Cheng et al. | |
| 2006/0284077 A1 | 12/2006 | Fissan et al. | |
| 2007/0043520 A1 | 2/2007 | Friedlander et al. | |
| 2007/0044580 A1 * | 3/2007 | Arcas et al. | 73/865.5 |
| 2007/0083127 A1 * | 4/2007 | Merrick et al. | 600/532 |
| 2007/0269093 A1 * | 11/2007 | Jones et al. | 382/131 |
| 2008/0017795 A1 * | 1/2008 | Ramiro Arcas et al. | 250/294 |
| 2008/0135745 A1 * | 6/2008 | Miller et al. | 250/282 |
| 2008/0149824 A1 * | 6/2008 | Miller et al. | 250/287 |
| 2009/0078064 A1 * | 3/2009 | Oommen | 73/865.5 |

FOREIGN PATENT DOCUMENTS

| | | |
|---|---|---|
| EP | 1 312 911 A1 | 5/2003 |
| EP | 1 678 802 A2 | 7/2006 |
| EP | 1 681 550 A1 | 7/2006 |
| GB | 2 346 700 A | 8/2000 |
| GB | 2 374 671 A | 10/2002 |
| GB | 2 378 510 A | 2/2003 |
| JP | 2007-127427 | 5/2007 |
| WO | WO 91/08459 | 6/1991 |
| WO | WO 99/41585 | 8/1999 |
| WO | WO 00/78447 A1 | 12/2000 |
| WO | WO 2004/009243 A1 | 1/2004 |
| WO | WO 2005/039780 A2 | 5/2005 |
| WO | WO 2005/100954 A1 | 10/2005 |
| WO | WO 2007/000710 A2 | 1/2007 |
| WO | WO 2007/016711 A1 | 2/2007 |

OTHER PUBLICATIONS

Anshuman A. Lall, et al., "On-Line Measurement of Ultrafine Aggregate Surface Area and Volume Distributions by Electrical Mobility Analysis: II. Comparison of Measurements and Theory", Aerosol Science, vol. 37, 2006 pp. 272-282.

K. Park, et al., "Tandem Measurements of Aerosol Properties—A Review of Mobility Techniques with Extensions", Aerosol Science and Technology, vol. 42, 2008, pp. 801-816.

* cited by examiner

MEASUREMENT SYSTEM FOR THE MULTIDIMENSIONAL AEROSOL CHARACTERIZATION

FIELD OF THE INVENTION

The invention relates to a method and a device for characterization of a totality of particles. More particularly, the particles can be aerosol particles, in particular microparticles and/or nanoparticles. The invention furthermore relates to uses of the device in aerosol monitoring. Methods and devices according to the present invention can be used, for example, in the fields of environmental analysis, protection at workplaces or process monitoring.

PRIOR ART

"Aerosols" is the name used below to mean, in general, mixtures of solid and/or liquid suspended particles (also referred to in gene-al as "particles" below) and gaseous media, in particular air. In general terms, the present invention relates to methods and devices for characterizing particles. Said aerosols are meant to be, in particular, aerosols with particles in the micrometer range, that is to say in the range <1000 µm, and/or, even preferably, in the nanometer range, that is in the range <1000 nm.

Examination and characterization of aerosols plays an important role in various areas of natural sciences, technology, medicine and daily life. By way of example, the surface characterization of aerosols and aerosol particles plays a critical role in the fields of environmental analysis and medicine, since the surface distribution and the surface morphology of aerosols can have a decisive influence on, for example, the toxicity of nanoparticles and, for example, the assessment of workplace pollution caused by aerosols and nanoparticles.

Knowledge of the structures of the particles, in particular of agglomerate structures, is indispensable for assessing workplace pollution of nanoparticles, parameterizing the inhalation-toxicological potential and process control in the synthesis of gaseous nanoscale particles. The on-line observation of particle formation is likewise of great interest in many other fields, for example in meteorology and climate research or aerosol physics.

In particular, gas-borne nanoscale particles, i.e. particles having a size of, for example, <1000 nm, or else micrometer particles, i.e. particles having a size of, for example, <1000 µm, are often in the form of agglomerates or aggregates, i.e. sintered agglomerates, of so-called primary particles. The structures of the agglomerates are here, for example, loosely linked in the manner of a chain and/or branched or maybe even spherically sintered.

In order to characterize the particles or aerosols, a large number of different devices and methods have been developed which enable, on-line or off-line, important statements about characteristics of the particles to be made. In the following text, "off-line" measurements are here measurements in which the measurement is effected independently of the gas flow, for example with time displacement and/or in a separate apparatus. In contrast, "on-line" measurements are those which are carried out directly and without any major time displacement, for example real-time measurements or measurements which are carried out at least nearly in real time.

The detection and counting of such particles already play an important role here, in particular in the field of nanoparticles. A large number of different types of particle counters are known and available commercially and are based on different measurement principles. For example, one measurement principle is based on detection by way of light, for example laser light. An example of such a laser particle counter is disclosed in WO 91/08459. Other particle counters or particle detectors for ultra small particles are based on charge effects, for example a particle counter disclosed in WO 2007/000710 A2. Other on-line measurement techniques, such as those based on scattered light methods (for example scattered laser light), are also known. Other counters and detectors are based on electrostatic principles, such as the particle sensor disclosed in WO 2007/000710 A2. It is also possible to use so-called condensation nucleus counters or condensation particle counters (CPC) in particular in order to be able to detect even very small particles, for example particles in the lower nanometer range, which is comparatively difficult using conventional light techniques. In these counters or detectors, the size of the particles is artificially increased, for example by way of depositing a film of condensate comprising butanol, by providing a condensate sleeve around these particles. The particles whose sizes are increased in this manner can then be detected comparatively easily. U.S. Pat. No. 4,790,650 discloses an example of a condensation particle counter.

Besides the pure detection and the counting of particles, classification, in conjunction with a corresponding detection of the particles, also plays a role. Conventionally, the particles are classified in an electrodynamic manner by categorizing the particles in accordance with their mobility, that is to say the ratio of the velocity of the particles to the force acting on the particles, into classes or fractions. In the case of electrically charged particles, in particular the so-called electrical mobility (often also referred to as Z) is used here, i.e. the ratio of the velocity of the particles to the electric field acting on the particles.

The mobility of a body moving in a liquid or a fluid (gas or liquid) is usually expressed by the so-called mobility diameter $d_m$, which is frequently also referred to as mobility-equivalent diameter. This is the diameter of a fictitious sphere which has said mobility in the fluid (for example the carrier gas used).

A large number of devices and methods have been developed for the classification, that means for separating the particles, for example in accordance with their mobility. One example is the so-called differential mobility analyzer (DMA). These analyzers are generally variable electric filters which, for example as a function of variable or fixedly prespecified geometrical dimensions and/or of variable or fixedly prespecified electric voltages, only allow particles of a specific electrical mobility from a particle flow to pass. Examples of such differential mobility analyzers are disclosed in WO 2007/016711 A1. Classifiers of this type are frequently connected to corresponding counters which directly allow the number or concentration of particles in the specific, filtered-out class to be counted. It is possible in this manner, for example, to determine concentrations and particle size distributions of the totality of the particles by changing the class. Such instruments are referred to, for example, with minor structural differences, as "DMPS" instruments (differential mobility particle sizers), SMPS (scanning mobility particle sizers) or FMPS (fast mobility particle sizers), without the difference between these principles being important in the following text. Examples of such classifier systems, which are connected directly to measuring instruments or counters, are disclosed, for example, in US 2006/0284077 A1, in US 2004/0080321 A1, in GB 2378510 A, in GB 2374671 A, in GB 2346700 A or in WO 99/41585.

Since charging particles or particle flows plays an important role in many methods or devices known from the prior art, a large number of devices have been developed which can produce defined charges on the particles. These devices, also referred to below as "charge state generators" or "chargers", can produce for example specific charge distributions (for example probabilities that a particle accepts one, two or more positive and/or negative elemental charges) or a fixedly pre-specified number of such charges on the particles. An example of such devices is disclosed in EP 1 678 802 A2, in WO 00/787447 A1 (there in connection with a DMA and a CPC) or in DE 198 46 656 A1. If the same number of positive and negative charges are produced, such charge state generators are frequently also referred to as neutralizers, such as is disclosed, for example, in U.S. Pat. No. 6,145,391.

As described above, in the on-line characterization particles, in particular aerosols, spherical equivalent particle sizes are generally assumed. This is, for example, a foundation of the abovementioned DMPS, SMPS and FMPS methods, since the mobility diameter $d_m$ is always used here. However, this could potentially result in significant errors if the ascertained characteristic values are used further. By way of example, different types of agglomerates cannot be differentiated. In addition, the error in the diameter also comes into play in the volume calculation of the particles to the power of three and thus also, for example, the mass calculation of the particles (if the density is known). The resulting errors in the determination of the mass concentration are significant. The inaccuracies of the known methods and devices also become very noticeable in the calculation of the particle surface areas, in which the errors in the diameter come into play to the power of two. This is a significant disadvantage of the known methods and devices, in particular in the field of toxicology, where the surface areas and surface distributions of the particles play a significant role. In addition, shape factors, in which for example the differences between rod shape, spherical shape, plate shape or similar shape differences come into play, can hardly be detected using the known methods.

Therefore, the on-line determination of the primary particle diameter, of the number of primary particles per agglomerate particle and of the shape factors of the agglomerates and other structure-specific parameters can overall hardly be carried out using the commercially available measurement methods. In order to determine those parameters, off-line measuring methods are conventionally used, in which some of the particles are taken from the totality, for example by way of samplers, in order to introduce them into other characterization methods. By way of example, these other characterization methods can be imaging characterization methods, for example scanning electron microscopy (SEM), transmission electron microscopy (TEM) or atomic force microscopy (AFM). Examples of samplers of this type, with which samples can be taken from the totality, are disclosed, for example, in WO 2004/009243 A1 or in JP 2007127427 A. The off-line methods described are, however, expensive and time-consuming and, in particular, do not permit on-line characterization and/or control, based on the evaluation of the characterizations, for example of process parameters, manufacturing parameters or safety measures in the field of protection at workplaces.

Further approaches for solving the abovementioned problems of the particle diameters are based on the fact that the particle diameters are determined, rather than a metrology method, on the basis of charging theories and theories relating to drag forces acting on agglomerates. An example of such a theoretical or semi-empirical method can be found in "On-line measurement of ultrafine aggregate surface area and volume distributions by electrical mobility analysis: I. Theoretical analysis", Aerosol Science 37 (2006) 260-271 by A. A. Lall et al. and in "On-line measurement of ultrafine aggregate surface area and volume distributions by electrical mobility analysis: II. Comparison of measurements and theory", Aerosol Science 37 (2006) 272-282 by A. A. Lall et al. The model described there combines a mobility analysis, carried out by means of a DMA or an SMPS, with calculations relating to the drag force acting on agglomerates and the charging efficiency of agglomerates. A theoretical approach is used which is based on a large number of assumptions which are restrictions at the same time. For example, it is assumed that the agglomerates comprise primary particles. The latter must be spherical and have a primary particle size a which is already known in advance. Furthermore, the surface of the agglomerates must be accessible. This means that primary particles do not cover each other which, for example, rules out aggregates having primary particles which are clearly fused together. The method can therefore not be applied to partially sintered agglomerates (aggregates). Overall, the described model therefore comprises a large number of model-based restrictions and assumptions which must be met so that the model provides realistic results.

OBJECT OF THE INVENTION

It is therefore an object of the present invention to specify a method and a device for characterizing a totality of particles, which avoid the above-described disadvantages of known methods and devices. In particular, the method and the device should be capable of on-line determination of characteristic target sizes and/or distributions of these target sizes as well, which depend on the exact particle geometry.

DESCRIPTION OF THE INVENTION

Said object is achieved by way of a method and a device having the features of the independent claims. Advantageous developments of the invention are illustrated in the dependent claims. The wording of all the claims is hereby included in the description by reference.

It is a fundamental idea of the present invention to combine devices and methods for characterizing particles, which devices and methods are known per se, such that at least one item of morphological information can be obtained in the process directly or at least indirectly. Said morphological information, referred to below as "morphological parameter", is intended to comprise an item of morphological information about an agglomerate state of the particles, to be more precise information about whether the particles are present in the form of loosely sintered (such as chain-type or branched) agglomerates, as partially sintered aggregates or as completely sintered aggregates or agglomerates. Accordingly, a categorization into morphological classes, for example, can be carried out. However, alternatively, or in addition, to an item of information information about a categorization into morphological agglomeration classes, the at least one morphological parameter can comprise further information. For example, the morphological parameter can comprise a number of primary particles per particle and/or have a primary particle size a and/or a primary particle size distribution and/or a shape factor, that is a factor which differentiates, for example, between plate shape, rod shape, tube shape or similar morphologies. It may also comprise an internal porosity and/or an agglomerate or aggregate porosity and/or an apparent density and/or agglomerate or aggregate density. Examples will be explained in more detail below.

As opposed to known, semi-empirical and theoretical approaches, such as the above-described publications of A. A. Lall et al., the invention thus provides a method, in which no assumptions or known information about the particle morphologies need to be used, but where a distinction can be made in a metrological manner between whether loosely sintered agglomerates, partially sintered aggregates or completely sintered, i.e. for example nearly spherical, agglomerates are present here.

Accordingly, a method for characterizing a totality of particles is proposed. A totality here is a quantity of particles, preferably of solid particles and/or droplets as suspended particles, wherein the quantity comprises a large number of said particles, preferably more than 100, in particular more than 1000, particles. This totality of particles can in particular be an aerosol, that is to say a totality of gas-borne particles, for example particles in air. The particles can in particular be microparticles and/or, preferably, nanoparticles. With respect to the definition of the terms "aerosol" and "microparticles" or "nanoparticles", reference can be made to the above description.

The method proposed according to the invention comprises the method steps illustrated below, which are preferably carried out in the illustrated order. However, orders other than the one illustrated are feasible. It is furthermore feasible that additional steps not listed in the method are carried out. It is additionally possible for individual method steps or groups of method steps to be carried out repeatedly or to be carried out such that they overlap at least partially in terms of time. The method comprises the following steps:

a) In a classification step, a class of the totality is selected, wherein the particles of the selected class have a prespecified mobility $d_m$.

With regard to the term "mobility", reference can be made to the above description. "Mobility" is to be regarded in broad terms and depends on the method used for the classification. In general, the term is meant to describe a connection between a movement state assumed by a particle as a reaction to an action of a force and the force itself. An example of this is a proportionality constant. The exact definition of the mobility can in particular depend strongly or the classification method used. An example of this is electrical mobility. In diffusion separators, it may be, for example, a diffusion equivalent diameter, in nano-impactors it may be an impaction equivalent diameter. It may in particular also be a mechanical mobility or, particularly preferably, an electrodynamic mobility. Alternatively, or in addition, to a specific mobility in the actual sense, however, it is also possible to use a variable which is uniquely related to the mobility. Therefore, the following text will express the term "mobility" using the mobility diameter, likewise denoted by the term $d_m$, without restricting further possible definitions. As illustrated above, an assumption in the case of this mobility diameter is that the particle is a sphere with the mobility diameter $d_m$.

When selecting the class, a fixedly prespecified mobility can be selected. Alternatively or additionally, which will generally be the case in practice, however, the prespecified mobility will comprise an open, half-open or closed interval of mobilities since even the most exact classification method always has a certain minimum resolution or since a mobility interval is intended to be selected deliberately.

In order to carry out the classification step, it is possible to use, as explained in more detail in the description of the device below, in principle all known classification methods and/or classification devices, for example the classification methods known from the prior art, which were described in the introduction. The use of electrostatic classification methods, such as using a DMA, is particularly preferred.

"Selecting" is here preferably to be understood as meaning that the selected class of remaining particles is separated from the totality in order to use this selected class separately. By way of example, the totality of the particles may be present in a storage container and/or a line system, where the selected class is output for, example into a selection container and/or a line system.

b) the proposed method furthermore comprises a counting step. In this counting step, a number N of the particles of the selected class is determined.

A "number" can in turn be understood to mean directly a number of a limited quantity of the selected class. This may be the case in particular if the particles of the selected class are made available, for example, in a closed vessel or if the selected class is closed in another manner. Alternatively, or additionally, to the determination of the absolute number of particles of the selected class, however, it is also possible in turn for a variable correlating directly to the number to be used, for example a particle flow rate. This is especially expedient if the selected class is continuously made available, for example in the form of a particle flow of the selected class being made available continuously. In this case a particle flow rate, that is to say, for example, a number of particles flowing through a flow pipe per time unit, a volumetric flow rate or the like can be stated as number N.

In order to carry out the counting step, it is possible in principle in turn for all known counting methods to be used, for example the above-described counting methods known from the prior art. For possible embodiments, reference is in turn made to the following description of the device or to the exemplary embodiments.

c) In a further method step (charge determination step), the charge Q of the particles of the selected class is determined.

Analogously to the number N of the particles, it is possible in turn to determine an absolute charge, for example an absolute charge of a closed quantity of the selected class of the particles and/or an absolute quantity of particles present in a pipe section of a line system or in a measurement chamber. The total charge or, if the number of the particles is known, an average charge can be determined here. Alternatively or in addition to a total charge, it is also possible in turn to use, analogously to the number N of the particles, correlating variables, for example the electric current I or the electric current density. For example, the charge flowing per time unit, i.e. the electric current I, can be determined. This is expedient in particular in the above-described case where measurements are carried out continuously, i.e, for example where the selected class is made available continuously. Here it is in turn possible in principle for all methods for charge determination known from the prior art to be used, for example the above-described methods. For example, a current I measured using an NSAM can be used directly as "charge Q". For further possible embodiments, reference is made to the description of possible devices mentioned below.

Natural mechanisms for example, such as the friction between the particles or the influence of impacts of the particles among one another, can be used in order to apply the charge to the particles of the selected class in the first place. As is explained in more detail below, it is particularly preferred, however, to carry out a separate charge generation step, in which a defined charge state of the selected class is established.

d) In a further method step (evaluation step), the at least one morphological parameter is determined from the charge C, the number N and the mobility $d_m$.

As described above, the morphological parameter comprises morphological information about an agglomerate state of the particles. This morphological parameter can comprise, for example, one or more numbers, vectors, matrices or else classifications into morphological classes. It is particularly preferred if the at least one morphological parameter comprises at least one of the following items of information: information about a categorization into morphological agglomeration classes, in particular a distinction between loose agglomerates, partially aggregated particles and aggregates; a number of primary particles per particle; a primary particle size a; a primary particle size distribution; a shape factor.

A primary particle size a is here understood to mean the size (this means for example the diameter and/or the radius) of primary particles from which the individual particle is made up. Such primary particles can generally be determined in conventional methods for example by way of off-line measurements, for example imaging off-line measurements, since in particular agglomerates are generally made up of, for example, round primary particles or other types of primary particles of simple geometry which can be determined easily (for example by way of image evaluation methods, for example by means of matching circles and/or other geometric base elements, such as squares and rectangles, to a two-dimensional image). In particular in the case of agglomerates, it can be assumed in a first approximation that the sum of the surface areas of the primary particles forms the surface area of the total particle and/or that the sum of the volumes of the primary particles forms the volume of the total particle. It is also analogously possible for example to estimate primary particle size distributions, for example by taking into account average primary particle sizes or primary particle size distributions within a particle.

As explained in more detail below, it is possible to establish an at least largely unique relationship between the variables Q, N and $d_m$ and the morphological parameter. This relationship can be obtained for example with the use of empirical, semi-empirical or analytical or theoretical considerations. By way of example, this relationship can be recorded in the form of a single-variable function, a multi-variable function, a graph, a value table, an electronic table or in similar form and used in method step d).

The evaluation step can also comprise the determination of more than one morphological parameters in a row. For example, it is possible using a known relationship between the variables Q, N and $d_m$ to conclude that a specific morphological class is present, for example a loosely agglomerated chain-type or branched state. This can be done for example, as explained below, when it is known for a prespecified $d_m$ that a specific morphological class effects a specific current per particle number, with the result that, if said current per particle number is actually measured, said class must be present. It is their possible to infer further morphological parameters from the knowledge that that morphological class must be present, which is usually assumed in conventional methods but is obtained in the method of the invention. Calibration functions can be used for this purpose for example, as explained in more detail below. It is possible, for example, to ascertain a primary particle size a or even a primary particle size distribution by means of a calibration function, which is valid for the ascertained morphological class, from the variables Q, N and $d_m$.

The above-stated problems of the methods and devices known from the prior art can be used elegantly using the proposed method. For example, the proposed method enables in particular an on-line characterization of the particle totality since, on the basis of the morphological parameter which can be determined on-line, a large number of further characteristic variables (referred to below as "target variables") can be determined, such as surface area, volume, primary particle number per agglomerate or aggregate, internal porosity and/or an agglomerate or aggregate porosity, apparent density, agglomerate or aggregate density or the like. It is thus possible to determine a large number of further structure parameters, in particular of nanoscale agglomerates, from the measurement variables, which can preferably be done without the aid of off-line analysis. As there is now a change from the simple sphere model of the mobility diameters towards a more realistic model which takes morphological aspects into account, for example a primary particle model, it is possible to determine the target variables with a significantly higher degree of accuracy than is possible in known methods and devices. In this manner, in particular toxicities, environmental compatibility, reactivities or similar properties of the particles can be predicted or estimated much better than is the case with conventional methods. Since the measurement can be carried out on-line, the proposed method can, in addition, be implemented without problems in a quick and cost-effective manner in various available measurement apparatuses, for example for open-loop and/or closed-loop process control.

The proposed method in its basic form illustrated above can be developed further advantageously in a variety of ways. The developments described below can be realized individually or in combination.

For example, the method illustrated above first describes the determination of the morphological parameter for the respectively selected class. However, as already explained, the method steps can also be repeated. This is useful in particular for a so-called scan, that is to say a method in which different classes with different mobilities $d_m$, i.e. mobilities which at least do not coincide completely) are selected one after the other. For these different classes, the morphological parameters are then determined in each case according to the described method, with the result that a primary particle size distribution as a function of the mobility $d_m$ can be ascertained. To this end, it is in particular possible to carry out the method steps a) to c) repeatedly. The evaluation step can likewise be repeated or all the variables ascertained in the method steps a) to c) can, in a subsequent overall evaluation step, be evaluated and converted to a distribution of the morphological parameter, for example a primary particle size distribution as a function of the mobility $d_m$. As already indicated above, it is possible then to infer from this distribution a large number of other distributions, for example a surface distribution, a primary particle size distribution, a volume distribution, a mass distribution, a shape factor distribution or similar distributions.

As likewise indicated above, it is possible, in the evaluation step, for a known relationship between the charge Q, the number N and the mobility $d_m$ and the morphological parameter to be used. This known relationship can, for example comprise at least one evaluation function (also referred to as calibration function below) which is determined by empirical, semi-empirical or analytical means. An evaluation function is, however, not necessarily to be understood here as a function in the conventional meaning, but the term can also comprise, for example, recorded calibration values, for example calibration values recorded in one or more tables or matrices and/or multi-variable curves of calibration functions, for example multi-variable curves which are parameterized with the morphological parameter (e.g. the primary particle size a). Examples of the determination of calibration functions are listed below.

It is in particular possible for the known relationship, which is used in the calibration function, to be determined for example by off-line methods. It is, however, alternatively or additionally, also possible to determine the relationship by means of on-line methods. Since the known relationship, which is ascertained in this manner, can subsequently be used in on-line methods, the abovementioned cost and time advantages of the proposed method are not decreased. For example the known relationship can be determined using a plurality of test particles, wherein for example the morphological class and/or the primary particle diameter a of the test particles can be determined in an off-line method, in particular an imaging method. The variables Q, N and $d_m$ of the test particles can subsequently be determined using a method with the method steps a) to c) according to one of the preceding claims and for example the primary particle diameter a can be ascertained by means of the relationship between the variables Q, N and $d_m$, using the obtained knowledge concerning the morphological class. The relationship can be ascertained, for example, using fit functions or the like.

As described above, it is furthermore particularly preferred if the proposed method comprises at least one charge generation step. In this charge generation step, it is possible for a defined charge state of the particles and/or of the selected classes to be established. A defined charge state is here understood to mean a state in which either the charge of each particle of the particles and/or of the selected class is known or in which a charge distribution of the particles or of the class of the particles is known. The charge state can be achieved by virtue of the fact that the particles have overall a total charge which is different from zero, or it is possible, depending on expediency, for an overall neutrality to be established, such that the positive and negative charges cancel each other out overall. The latter case is often also referred to, somewhat confusingly, as "neutralization", since neutrality prevails overall, although charged particles are still present.

As explained below likewise by way of example, the charge generation step can be expedient at different places in the proposed method. For example, the charge generation step can be carried out in particular before or during the classification step and/or before or during the charge determination step. In order to carry out the charge generation step, it is in turn possible in principle to use all methods known from the prior art to establish a defined charge state, for example using the above-described methods and devices known from the prior art, in particular the so-called chargers. Thus, e.g., the charge generation step may comprise the use of ionized particles or ionized particle beams and/or the use of ionizing radiation, such as ionizing particle rays and/or ionizing electromagnetic radiation. Preferably, the charge generation step of the particles comprises the use of radioactive radiation and/or electromagnetic radiation. The charge generation may be performed in a direct or indirect way. Thus, the charge may be generated in and/or transferred to the particles directly, such as by directly ionizing the particles. Alternatively or additionally, an indirect way of charging may be used. Thus, the charges may be generated in or on separate carriers, such as on carrier gas molecules, e.g. on air molecules, and, subsequently, transferred from the charged carriers onto the particles, such as by diffusion of the charged carriers towards the particles. The latter principle is generally known as "diffusion charging" and is a preferred charging mechanism under the present invention. Thus, diffusion charging provides the advantage of the charging being widely independent from the material of the particles. Making use of diffusion charging, silver particles for example generally will be charged the same way as polymer particles or particles made of other types of insulating materials. Typically, besides the carrier (such as a carrier gas), diffusion chargers comprise one or more radioactive materials, preferably materials emitting rays such as alpha- and/or beta-rays which are able to ionize gas molecules. As an example, $^{85}$Kr and/or $^{210}$Po may be named. However, additionally or alternatively, other types of ionizing rays and/or beams and/or means may be used, such as gamma radiation and/or ultraviolet radiation and/or ionized particle beams and/or plasmas. Generally, the chargers can also be integrated fully or partially in other devices, for example in classification devices and/or devices for determining the charge.

In order to simplify evaluation, it is first possible to form a sensitivity S from the charge Q and the number N. As described above, the variables Q and N can in turn also comprise or be variables which directly correlate with the actual charge or the number. For example, the sensitivity can comprise a current, divided by a number. In general, the sensitivity S should be a prespecified function of the charge Q and the number N, in particular a quotient of the charge Q and the number N.

As described above, for example a known relationship between the charge Q, the number N and the mobility $d_m$ and the at least one morphological parameter can be used in the evaluation step. By way of example it is also possible to use, rather than said relationship, a relationship between the sensitivity S and the mobility $d_m$ and the morphological parameter. In this manner it is also possible, even when classifying only a single class, i.e. without using a scan, to determine the morphological parameter. Alternatively or in addition, however, a scan can also be carried out and the morphological parameter can subsequently be determined by a fit function. The charge Q and the number N (or the sensitivity S) for a plurality of different classes with different mobility $d_m$ are determined in the process. In the evaluation step for determining the primary particle size a and/or other morphological parameters, a fit function, which is parameterized with the at least one morphological parameter, for example the primary particle size a, is fitted to the charge Q and the number N or the sensitivity S formed from the charge Q and the number N in order to determine the morphological parameter, for example the primary particle size a. Examples of such a fitting operation are described in more detail below.

As shown above, the knowledge of the morphological parameter can be used to determine further target variables, or distributions, which characterize the totality of the particles and correlate with the morphology. Said target variable X, which at least partially characterizes the selected class of the particles, can comprise for example a surface area of the particles or of the particles of the selected class, a volume of said particles, a mass of said particles, a shape factor of said particles, a number of primary particles per particle or agglomerate or similar possible target variables. Here, this target variable can be determined such that it is determined for different classes with different mobilities $d_m$, as a result of which a target variable, in particular a target variable distribution as a function of the mobility $d_m$ can be ascertained.

As illustrated above, the proposed method can be used in particular as on-line method, that is to say a method which provides results in near real-time in a process without said process (for example a manufacturing or production method) having to be interrupted significantly for this purpose. Nevertheless, the proposed method can be expanded optionally by off-line measurements. This can be advantageous, for example, for carrying out reference measurements, for ascertaining the relationships (illustrated above) for the evaluation step or for occasionally monitoring the plant. To this end, the proposed method can preferably comprise a sampling step in which a quantity of the particles of a selected class is removed. By way of example, it is possible to remove particles for each selected class or also only for one or more specific selected classes. The quantity of removed particles can be investigated in an alternative characterization method, in particular an off-line characterization method. This characterization method can in particular be an imaging method and/or a chemical analysis method. It is possible in this manner to ascertain for example morphological parameters such as morphological classes, primary particle sizes or the like using an optical microscopy method, a scanning electron microscopy method, a transmission electron microscopy method, an atomic force microscopy method or other known imaging methods or combinations of such imaging methods.

In addition to the proposed method, furthermore a device for characterizing a totality of particles is proposed. The device can be designed in particular for carrying out a method according to one or more of the embodiments described above. With respect to possible embodiments and definitions, reference may accordingly be made to the above description. In order to carry out such a method, the device can comprise in particular a controller. This controller can, for example be in the form of a centralized or decentralized controller and can, for example, comprise an electronic controller, in particular a data-processing machine. Said data-processing machine can comprise, for example, a microcomputer and/or a personal computer, including one or more processors, memories, input and output means and/or similar appliances which are usually present in data-processing machines.

According to the method steps a) to d), the device comprises a classifier, a counter, a charge meter and a calibrator. Here, the classifier selects a class from the totality, the counter determines the number N of the particles of the selected class, the charge meter measures a charge of the particles and the calibrator determines the at least one morphological parameter, for example the morphological class, the aggregation class, the primary particle size a or combinations of a plurality of morphological parameters. Classifier, counter, charge meter and calibrator can here be in the form of separate but preferably directly connected elements (for example connected to one another via a line system). The elements can, however, also be fully or partially integrated with one another, such that for example the classifier and the counter can be designed fully or partially with identical components. The calibrator can comprise in particular a data-processing machine, since the tasks of the calibrator lie in particular in the area of data evaluation. The calibrator can furthermore also comprise interfaces by means of which for example input and output operations can be undertaken, wherein for example morphological parameters (for example primary particle sizes or primary particle size distributions) or target variables or target size distributions derived therefrom can be queried.

As explained above, the device can comprise in particular a line system. This line system is intended to be designed for guiding a flow of the particles, in particular a volume flow and/or mass flow of the particles. For this purpose, the particles can be present, as explained above, in the form of gas-borne particles, in particular as aerosol. By way of example, a carrier gas can be used. Said elements of the classifier, the counter and the charge meter are intended to be connected to the line system. The classifier in the line system can in particular be connected upstream of the counter and the charge meter. In addition, the line system can, of course, comprise a further one or more gas inlets, for example for introducing the primary particles and/or one or more carrier gases. Furthermore, the line system can also comprise measurement and/or control devices, for example measurement devices for determining a volumetric flow rate, pumps, flow meters, flow controllers, valves or the like.

The counter and the charge meter can here in principle be connected to one another in series. It is particularly preferred, however, if the counter and the charge meter are arranged in parallel branches of the line system. Here, a branching ratio between a first partial flow rate through a first branch, to which the counter is connected, and a second partial flow rate through a second branch, to which the charge meter is connected, can be known or can be set. It is particularly preferred if the first and the second partial flow rates are equivalent. In order to ensure a flow equalization between the first partial flow rate and the second partial flow rate and the total flow rate of the particles flowing through the line system, it is possible for the line system to additionally comprise at least one bypass line, wherein the bypass line is designed for guiding a bypass flow past the counter and/or the charge meter. It is thus possible to adjust the individual partial flow rates in an optimum manner.

As described above within the framework of the method, it can occasionally be expedient to carry out an off-line analysis, in addition to an on-line characterization of the totality of the particles. The device can accordingly furthermore comprise at least one sampler, in particular a sampler which is connected to the line system. The sampler can be designed in particular for removing a quantity of the particles of a selected class and introducing them into an alternative characterization method, in particular an imaging method. The sampler can here in principle use any desired means of removing particles. By way of example, the samplers which are described in the introduction and known from the prior art can be used for depositing particles for example on a substrate. They can be deposited, for example, on one or more transfer substrates which are subsequently introduced into the imaging method.

Further preferred exemplary embodiments relate to the preferred design of the classifier, the counter and the charge meter. These devices can, for example, in turn comprise all such devices and implement all those principles which are known from the prior art. In the classifier, it is particularly preferred if it has at least one of the following devices: an electrostatic classifier, that is to say a classifier in which the classification is carried out by way of separation by an electric field and optionally one or more openings or apertures. In particular, said electrostatic classifier can comprise one or more differential mobility analyzer(s) (DMA). It is also alternatively or additionally possible, however, for other types of classifier to be used, such as diffusion classifiers (e.g. diffusion separators), particle mass spectrometers, nano-impactors or similar classifiers or combinations of classifiers.

The counter can comprise, in particular, a condensation particle counter and/or a condensation nucleus counter, that is to say a counter in which the size of the particles is first artificially increased, for example by means of condensation, in order to simplify subsequent counting thereof. Alternatively or in addition, the counter may also comprise a laser counter and/or another type of optical counter. Alternatively or in addition, the counter can also comprise at least one electrostatic counter which is designed for inferring a particle number and/or a particle flow rate from an electric current caused by charged particles. Other types of counters or combinations of the counters mentioned and/or other counters can, of course, also be used.

With respect to the charge meter, it is particularly preferred if it comprises a current measurement device for measuring an electric current caused by charged particles. Alternatively or in addition, however, it can also comprise an electrometer, in particular a Faraday cup electrometer. It is particularly preferred if it comprises, alternatively or in addition to the devices mentioned, a particle surface area meter, in particular a nanoparticle surface area monitor (NSAM). Such a nanoparticle surface area monitor is described, for example, in US 2006/0284077 A1 which is mentioned in the introduction and comprises in principle the measurement of an electric current. Such nanoparticle surface area monitors are commercially available.

As described above, the device can furthermore comprise at least one charge state generator which is designed for imposing a defined charge state on the particles and/or the selected class of the particles. This charge state generator can in particular be connected upstream of the classifier or comprised in the classifier and/or can be connected downstream of the classifier. The charge state generator can, for example, be a bipolar charger, a neutralizer, a charge state generator which is based on a radioactive radiation source; a charge state generator which is based on an electric field; a charge state generator which is based on a light beam, in particular a UV light beam; a charge state generator which is based on a corona discharge or combinations of the charge state generators mentioned and/or other charge state generators.

The method and device described, in each case in one or more of the illustrated embodiments, can be used advantageously in different ways. The use of the device for aerosol monitoring in the field of environmental analysis and/or of protection at workplaces or toxicology is particularly preferred. The device can also be used alternatively or in addition for aerosol monitoring in the area of process control, wherein a method is used which is based on using at least one aerosol, wherein the device is used to monitor the aerosol.

In general, the invention can preferably be used in the area of process monitoring and in the area of process control, in particular in gas phase processes. Examples to be mentioned are the production of carbon nanotubes (CNT), the flame and plasma synthesis (for example of metal oxides and/or mixed oxides), desublimation, hot wall reactors, dispersing and drying methods, gas phase separation processes (chemical vapour deposition (CVD) and/or chemical vapour synthesis (CVS)) or similar processes. In these process the method and device described can be used to carry out process control on the basis of the desired particulate structures (for example length and diameter of the CNTs, primary particle size and primary particle fraction per agglomerate, sintered state, agglomerate surface area, agglomerate volume etc.).

It is furthermore not, or only with difficulty, possible in conventional methods to determine mass concentrations of nanoscale particles gravimetrically. The method proposed above and the proposed device can be used to determine a mass concentration of nanoscale gas-borne particles, in particular with respect to future emission and immission limit values of fine dusts. Furthermore, structural parameters of nanoscale particles, in particular the abovementioned target variables, can be correlated with the toxic potential, for example or the field of protection at workplaces. This is an advantage in particular in administrations, institutes and specialist sections as well as in the field of inhalation toxicology.

EXEMPLARY EMBODIMENTS

Further details and features follow from the description below of preferred exemplary embodiments in conjunction with the subclaims. Here, the respective features can be implemented on their own or together with others in combination. The invention is not restricted to the exemplary embodiments. The exemplary embodiments are illustrated schematically in the figures. Here, identical reference numerals in the individual figures denote identical elements or elements which have the same or analogous functions.

Specifically:

Figure 5:
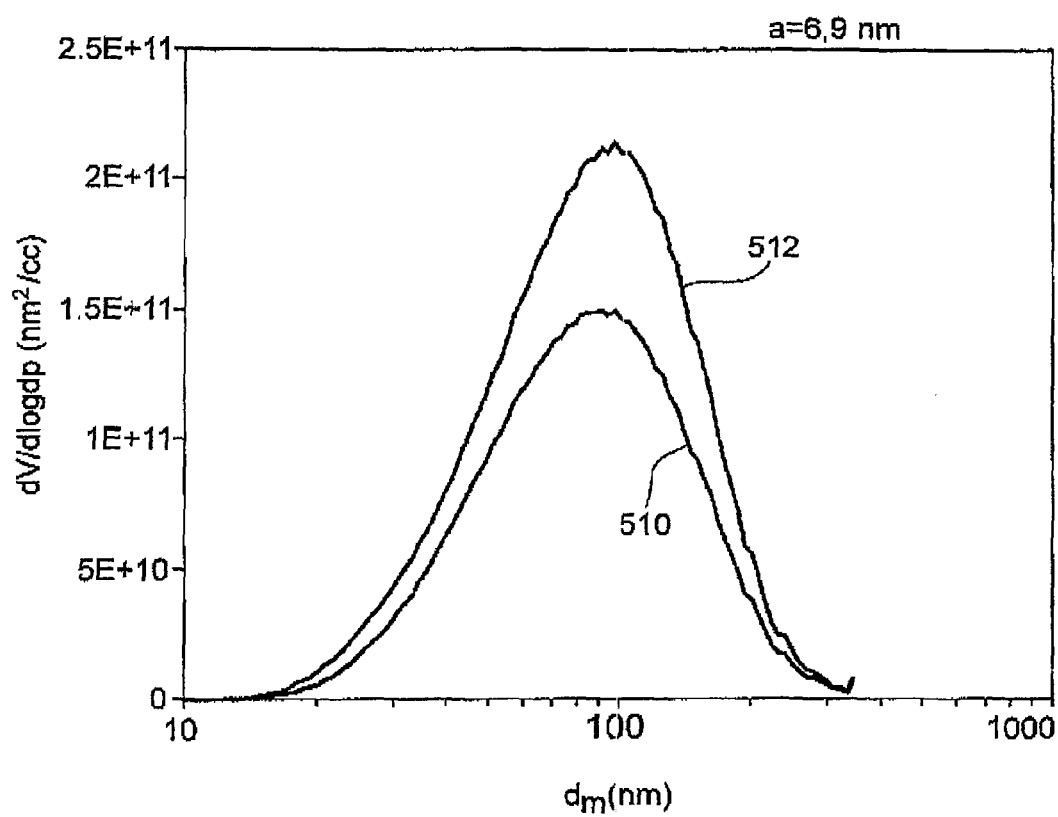
Figure 6:
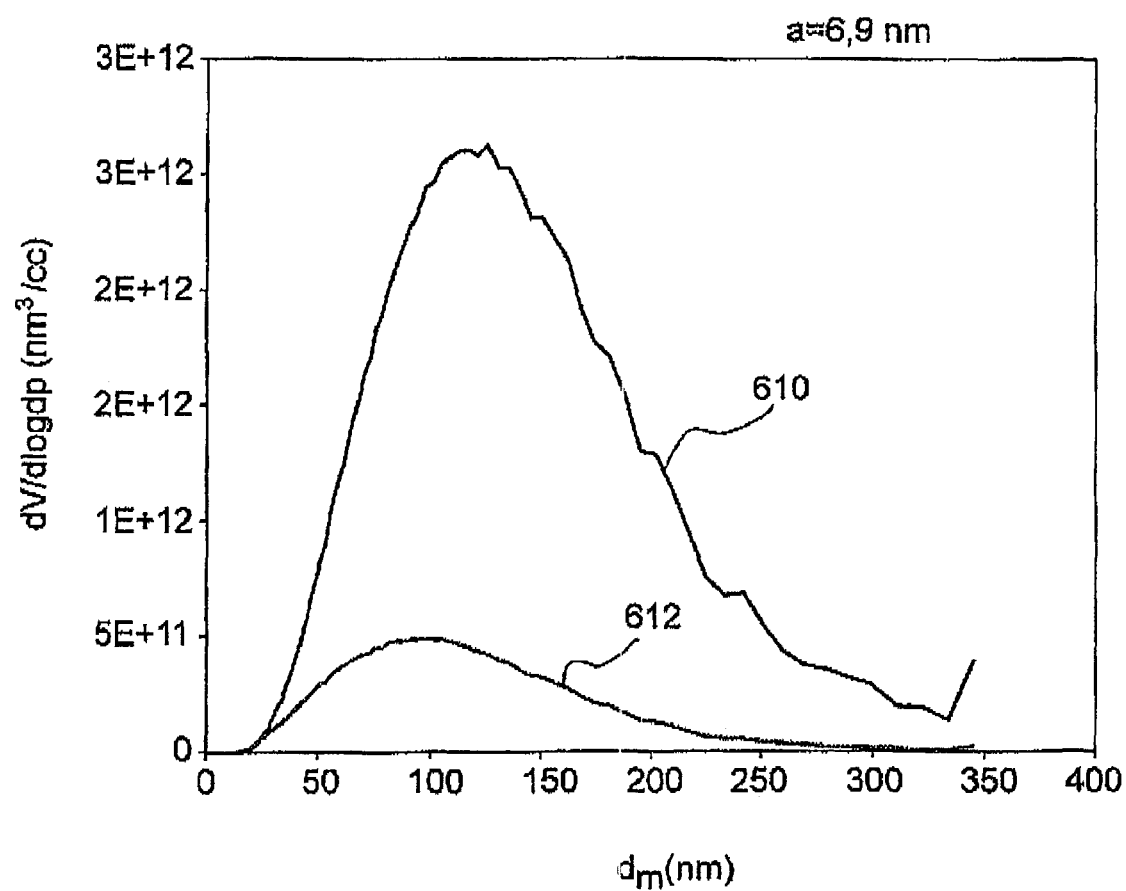

FIG. 5 shows a comparison of a surface distribution determined according to conventional methods with a surface distribution of an aerosol which is determined according to the invention; and FIG. 6 shows a comparison of a volume distribution of an aerosol which is determined according to a conventional method with a volume distribution of an aerosol which is determined according to a method according to the invention.

Figure 1:
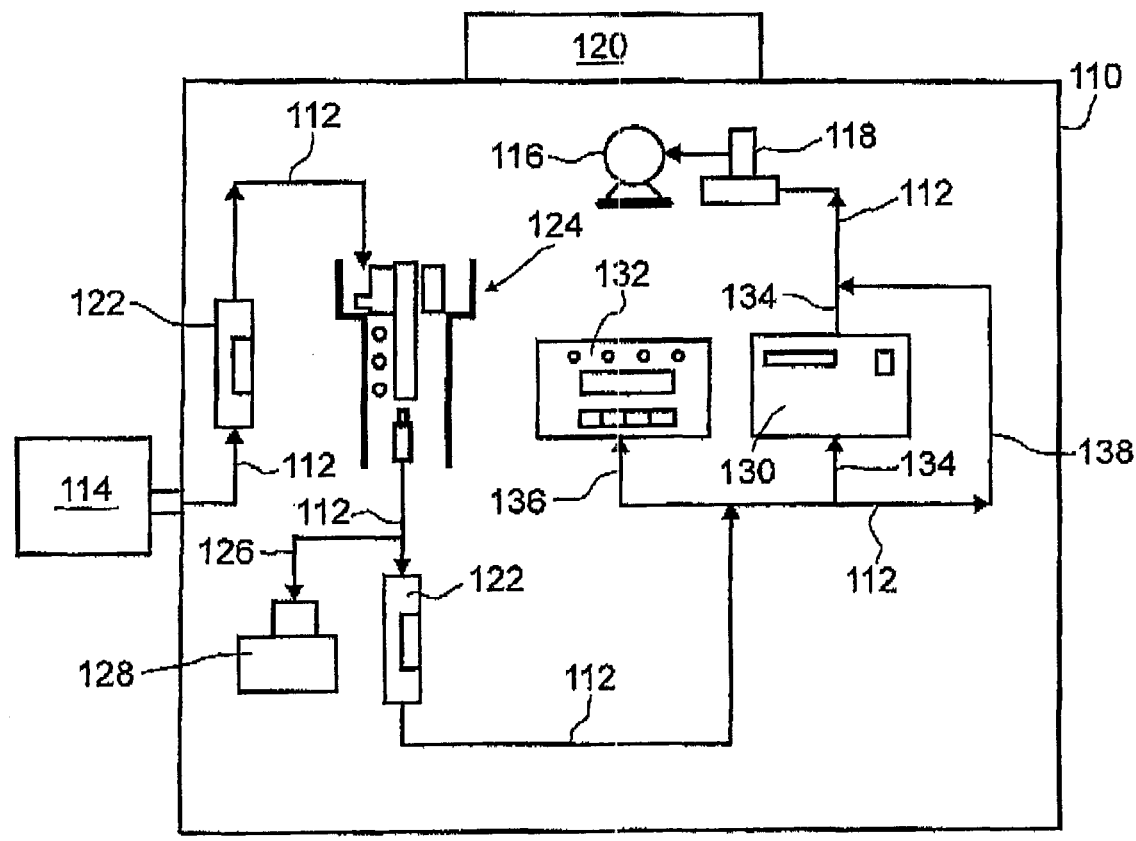
FIG. 1 shows a schematic of a device according to the invention.

FIG. 1 schematically illustrates an exemplary embodiment of a device 110 for characterizing a totality of particles according to the invention. It is assumed in the following text, without restricting the possibility of further embodiments, that the totality of particles means particles of an aerosol. As a model system, sintered agglomerates of silver nanoparticles are considered below. However, other particles or aerosols are, of course, also possible.

In the exemplary embodiment illustrated in FIG. 1, the device 110 has a common line system 112, to which aerosol can be supplied via an aerosol inlet 114. Said aerosol inlet 114 can have various designs, so that different connections for carrier gases, particles, aerosols or similar can be provided, for example. The particles or the aerosol are sucked through the line system 112 using a pump 116 which is regulated, for example, at a constant volumetric flow rate. It can be regulated, for example using a mass flow controller (MFC) 118. The flow rate can, for example, be adjusted by way of a controller 120 of the device 110, to which, for example, measurement signals of individual or all of the components illustrated in FIG. 1 can be delivered and which can output control and/or regulating signals to individual or all of the components of the device 110 illustrated in FIG. 1. This controller 120 can, for example, comprise a microcomputer and/or a personal computer.

In the line system 112, first a charge state generator 122 is arranged, which is connected to the aerosol inlet 114 via the line system 112. The charge state generator 122 can, for example be in the form of a bipolar charging source and can, for example, be equipped with a radioactive source, for example a $^{85}$Kr source. However, other embodiments are also possible.

The charge state generator 122 is connected to a classifier 124 again via the line system 112. This classifier 124 is, in turn illustrated only symbolically in FIG. 1. In the present exemplary embodiment, this classifier can be in particular a differential mobility analyzer (DMA), that is to say a classifier 124 which can select a class with a prespecified mobility $d_m$ from the aerosol, for example by setting a particular aperture geometry and/or a voltage and/or an electric field. Selection of the class can, for example, in turn be controlled by the controller 120 such that the mobility $d_m$ which is selected can be prespecified by means of the controller 120. In a similar way, it is possible for mobility scans to be carried out, for example, that is to say scans in which different classes are selected one after the other. Such a scan can be controlled, for example in the classifier 124 itself and/or control can again be prespecified by means of the controller 120.

The classifier 124 is connected to a second charge state generator 122 again via the line system 112, which preferably only the selected class of the aerosol can now enter. This second charge state generator can again be a bipolar charger. This second charge state generator 122, downstream of which is connected the classifier 124, frequently acts as a so-called "neutralizer", since here a charge balancing occurs within the selected class in order to establish a neutrality of the selected class overall.

A partial line 126 which is connected to a sampler 128 branches away from the line system 112 between the classifier 124 and the charge state generator 122. Said sampler can, for example, be in the form of a nanoparticles aerosol sample and can, for example, comprise one of the above-described samplers. This sampler 128 should be designed, in particular, for enabling samples for an off-line characterization of the selected class or a plurality of selected classes of the aerosol. To this end, the sampler 128 can, for example, comprise one or more sample carriers to which one or more particles of one or more classes of the aerosol can be applied in order to be subsequently introduced into an imaging method, for example. The partial line 126 can, just like, for example, one or more of the remaining sections of the line system 112, be equipped with one or more valves for controlling, for example, a sampling operation. Said valves can, in turn, be operated via the controller 120, with the result that, for example, the sampling can also be controlled by means of the controller 120.

The second charge state generator 122, which is connected downstream of the classifier 124, is connected to a counter 130 and a charge meter 132 again via the line system 112. Said counter 130 and the charge meter 132 are here connected in parallel. To this end, the line system 112 branches into a first branch 134, which leads to the counter 130, and a second branch 136, which leads to the charge meter 132. The ratio of the partial flow rates through the two branches 134, 136 is preferably known or can be set. This can be done, for example, by way of appropriate apertures and/or valves, which can be adjusted, for example, again by means of the controller 120. It is particularly preferred if the partial flow rate through the two branches 134, 136 can be adjusted such that they are equal.

The exemplary embodiment illustrated in FIG. 1 furthermore provides a bypass line 138 which guides a bypass flow to the pump 116 past the counter 130 and the charge meter 132. In the exemplary embodiment illustrated in FIG. 1, the counter 130 is connected, at its downstream side, again to the bypass line 138, so that the partial flow flowing through the first branch 134 is sucked through the counter 130 by means of the pump 116.

The counter 130 can, for example, as illustrated above, comprise a condensation particle counter (CPC). The charge meter 132 can, for example, comprise a nanoparticle surface area monitor (NSAM), such as an NSAM from TSI GmbH in Aachen, Germany, which measures the charge output of the particles as electric current. Other embodiments are, however, also possible in each case. Without restricting further possible embodiments, the classifier 124 is in the following text also referred to as DMA, the counter 130 also as CPC and the charge meter 132 also as NSAM.

The particles are sucked using the pump 116, which is adjusted to a constant volume flow rate, firstly through the first charge state generator 122, which is connected upstream of the classifier 124 and brings the particles to an electrically defined charge state. As described above, this can be a bipolar charging using a radioactive source, for example.

Subsequently, the particles are classified into monodisperse fractions of equal size, i.e. of the same mobility, using the classifier 122 which operates, for example, in an electrostatic manner. Said fractionation can be modified, for example, by varying the electric voltage or the electric field, with the result that, as illustrated above, an entire size range or range of fractions can be measured within the framework of a scan.

The class or monodisperse particle fraction this selected is subsequently preferably brought again to an electrically defined charge state in the second charge state generator 122, which is connected downstream of the classifier 124 and can, for example, have the same design as the first charge state generator. Subsequently the gas flow is divided and guided to the charge meter via the second branch 136. The charge which is located on the particles is detected in the charge meter. Since the electric charge on the particles correlates with the particle surface area, the particle surface area of the monodisperse fraction or class is thus also directly or indirectly detected.

A second gas flow is guided via the first branch 134 into the counter 130. As described above, a condensation nucleus counter or an electrometer, inter alia, is suitable for nanoscale particles.

The illustrated device can thus be used to prespecify or set the mobility $d_m$ and to measure the charge Q and the particle number N of the fraction or class thus selected by means of the charge meter 132 and the counter 130. It should be noted that the counter 130 and the charge meter 132 are also illustrated in FIG. 1 as separate elements, but that they can also be designed fully or partially with identical components.

In addition to the variables $d_m$, Q and N, which can thus be determined on-line, it is possible to carry out an off-line analysis using the optional sampler 128, which can be operated at the same time but can also be integrated in the line system 112. Such particles which are separated depending on their size can, for example, be used for a chemical analysis, an off-line REM/TEM analysis; or similar types of analysis.

A possible exemplary embodiment of the method according to the invention will be described below with reference to the illustrations in FIGS. 2A and 2B. Here, reference is made to a device 110 according to the exemplary embodiment in FIG. 1. However, other types of devices 110 can in principle also be used within the framework of the method according to the invention.

Figure 2A:
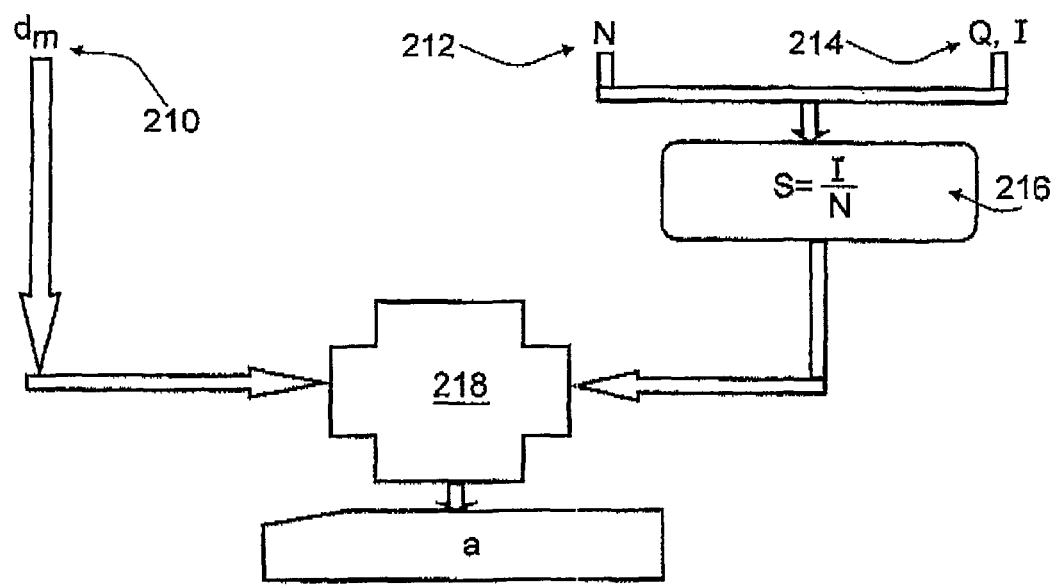
FIGS. 2A and 2B show flowcharts of exemplary embodiments of a method according to the invention.

The reference numeral 210 symbolically denotes in FIG. 2A a classification step. In this classification step 210, a mobility, here indicated for example by the mobility diameter $d_m$, is, as described above, prespecified for example by means of the DMA of the classifier 124.

Furthermore, the reference numeral 212 symbolically denotes a counting step in FIG. 2A. This counting step 212, which can be carried out for example using the counter 130 or the CPC, determines a number N of the classified particles. As illustrated above, this number N can also be an analogous variable, for example a particle flow rate, that is to say a number of particles which flows, per time unit, through the first branch 134 and directly gives information about the total number of the classified particles, that is to say for example of the agglomerated particles of a particle fraction.

The reference numeral 214 symbolically denotes in FIG. 2A a charge determination step. In this charge determination step, the charge of the classified particles is determined, for example using the charge meter 132 or NSAM. In practice, however, in particular if for example an NSAM is used, rather than the charge, a variable which correlates directly with the charge is determined, in general the current I. As illustrated above, the term of "charge" should encompass this. Therefore, the current I is partially equated with the charge Q below.

In a further method step, which is symbolically denoted in FIG. 2A by the reference numeral 216, a sensitivity S is ascertained from the two measurement variables N and I (or Q), with the sensitivity S being a function of said two measurement variables. The quotient of the current I and the number N, i.e. I divided by N, has proven here particularly useful. In principle, the ascertainment of the sensitivity 216 is an optional method step, but one which can facilitate the subsequent evaluation and calibration. The sensitivity can be ascertained, for example, using one or more electronic components, for example using a divider, or, for example, in a fully or partially computer-supported manner, for example again in the controller 120, for example program-controlled by one or more computer programs.

Then, in principle one or more target variables X can be determined from the now known mobility diameter or mobility $d_m$ of the agglomerated particles, from the electric current I or the charge Q and from the number N by way of an appropriate combination of said signals or variables. The number distribution, the surface distribution or the volume distribution and the shape factor can, for example, be derived from loose and sintered agglomerates. Furthermore, the primary particle size and the number of primary particles per agglomerate and/or a mass and/or a mass distribution can be calculated, for example.

The further evaluation, using the prespecified variable $d_m$ of the mobility, and the measurement variables N and Q or I is effected in the method of the invention according to FIG. 2A in an evaluation step. This evaluation step is symbolically denoted by the reference numeral 218 in FIG. 2A. The aim of this evaluation step 218 is to ascertain at least one morphological parameter, for example the primary particle size a. The evaluation step 218 can again be carried out in a fully or partially computer-supported manner, for example again using the controller 120 of the device 110 in FIG. 1. To this end, this controller can, for example, comprise a data-processing machine, which can be appropriately equipped in terms of program technology.

Figure 3A:
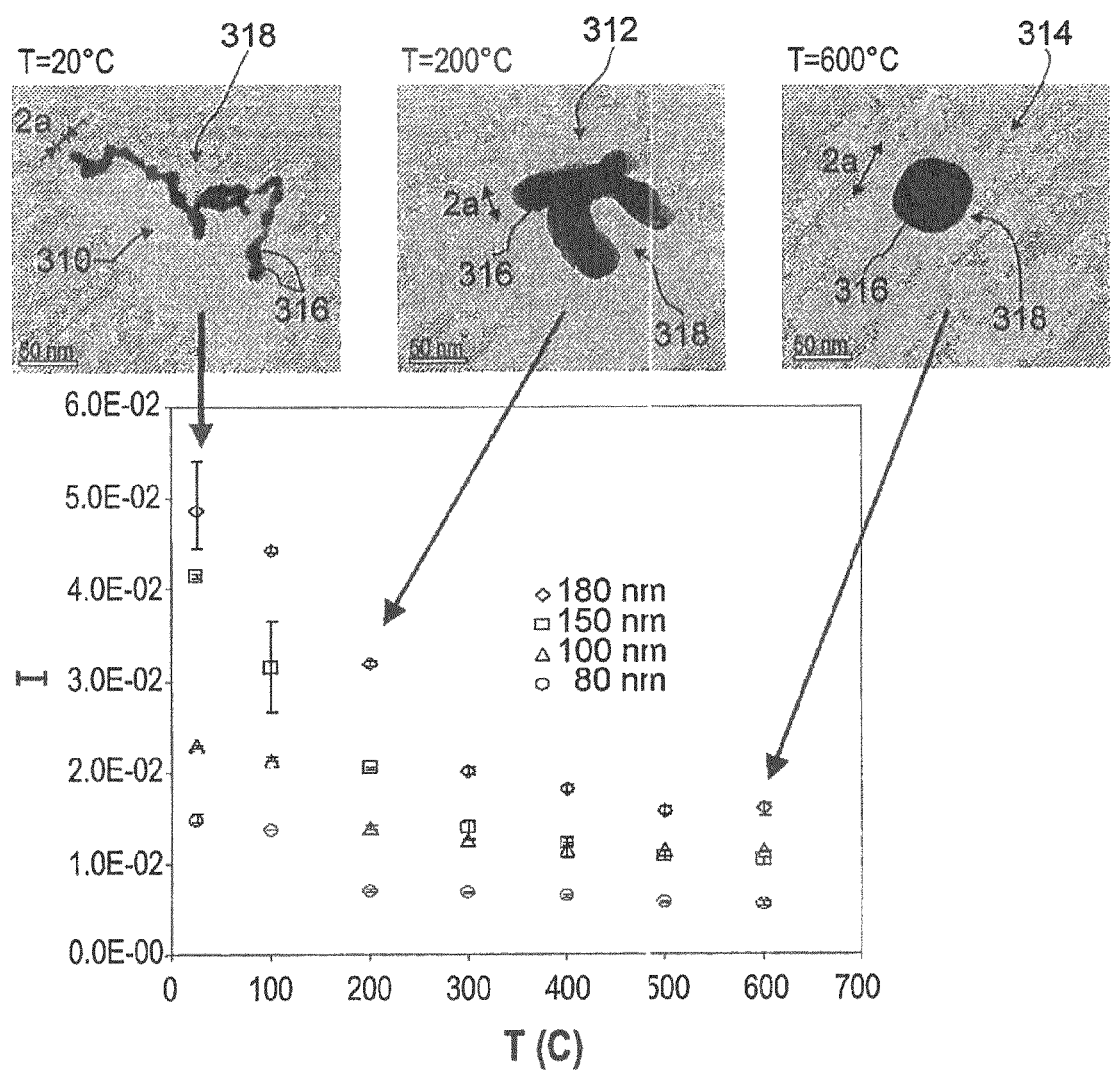
FIG. 3A shows an exemplary illustration of the influence the primary particle size has on the current in a charge meter.
Figure 3B:
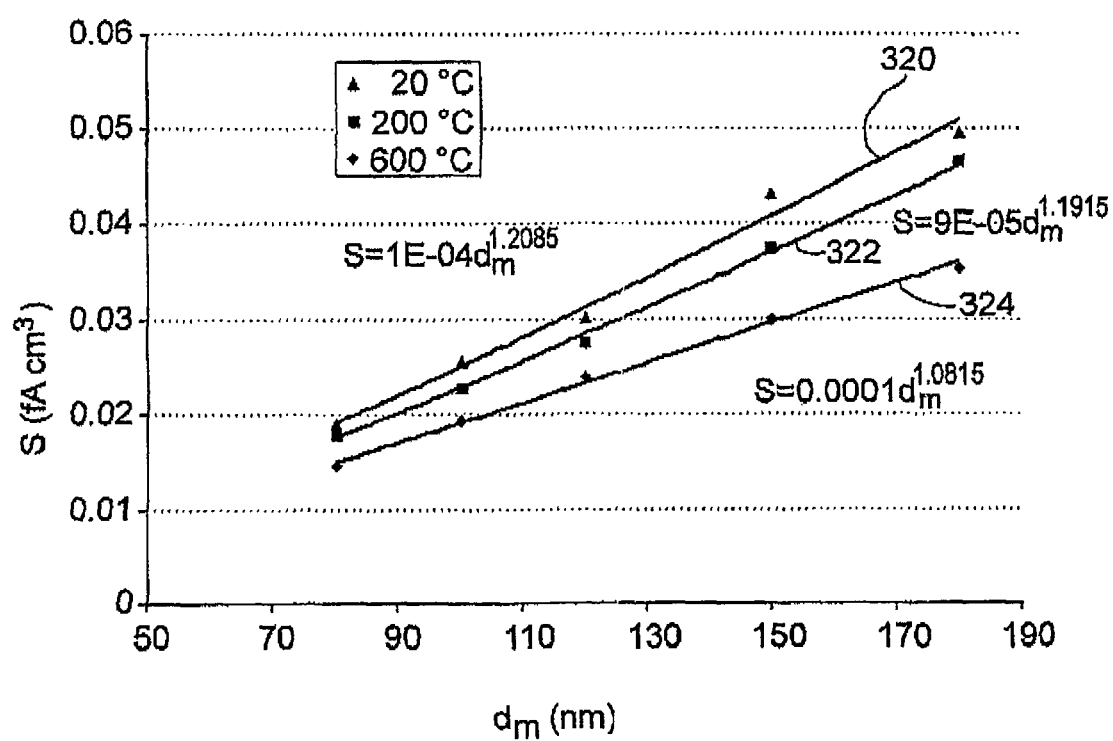
FIG. 3B shows examples of calibration curves.

For the purposes of clarifying a possible embodiment for carrying out the evaluation step 218, reference is made to FIGS. 3A and 3B.

By way of example, FIG. 3A shows that there is a relationship between the signal Q or I, which is measured using the charge meter 132 (for example an NSAM signal), and the morphology of agglomerated particles. In the graph, the NSAM signal is plotted in the form of a current I (for example in fA per particle) as a function of a sintering temperature T (measured in ° C.) for a known particle number, that is to say the temperature at which the particles were sintered. The different symbols denote particles of different overall size, i.e. different nobility diameter, with values between 180 nm and 80 nm having been used.

Partial pictures 310 to 314 show off-line images of the particles or agglomerates at three different sintering temperatures, which are selected as examples. These images were obtained using imaging methods, with transmission electron microscopy having been used in the present case. However, other imaging methods can also be used. By way of example, these particles in the device 110 according to FIG. 1 can be removed from the line system 112 using the sampler 128 and introduced into the imaging method.

As can be seen in the partial pictures 310 to 314, the sintering temperature has a critical effect on the shape of the agglomerate. At a sintering temperature of only 20° C., in the prespecified model system, the agglomerates are merely in the form of loose linkages of approximately spherical partial particles, which are also referred to below as primary particles 316. Depending on the type of the particle system used, the primary particles 316 can, however, also have a different geometry, for example a square geometry, a plate-type geometry, a rod-type geometry or the like. While in the case of a sphere as primary particles 316 the diameter can serve as primary particle size a, in the case of other geometries of the primary particles 316 other variables characterizing the size of the primary particles 316 must be used, such as an edge length. By means of manual evaluation or evaluation using imaging methods (for example by fitting circles to the primary particles 316 in the image 310), it is possible to determine the primary particle sizes a and their average values or mean values off-line. In the following text, the radius of the primary particles, assumed to be spherical, is regarded as the primary particle size.

As is evident from a comparison of images 314 and 316 (sintering temperatures of 200° C. and 600° C., respectively) with the first image 310 (sintering temperature 20° C.), the morphology of the particles changes, and the primary particle size a increases with rising sintering temperature. The size of the primary particles 316 can again be determined for example manually or by computer-supported image evaluation methods. At very high temperatures, the primary particle size a approaches a constant value, since the shape of the primary particles 316 approaches a shape of a single sphere.

The partial pictures 310 to 314 show different morphological classes. Thus, the particles 318 in partial picture 310 generally are referred to as "agglomerates". Agglomerates generally comprise an agglomeration of primary particles 316 being "linked" to each other mostly by Van der Waals-forces. Contrarily to the agglomerates shown in partial picture 310, the particles 318 in partial picture 314 are representatives of the morphological "antipodes", showing a more or less spherical shape. In between, the particles shown in partial picture 312 generally are referred to as "aggregates". Therein, the primary particles 316, which already are rather difficult to resolve, are linked to each other mostly by material bridges.

The three morphological classes shown in the partial pictures 310 to 314 may be numerically characterized using one or more morphological parameters, such as the primary particle size a of the primary particles 136 and/or other morphological parameters. Thus, inter alia, a morphological parameter k may be used, which, in the following, will be referred to as a "shape factor", even though it may not necessarily describe a geometric or morphological shape in strictu sensu. Alternatively or additionally, other morphological parameters may be used. The shape factor k describes the degree of sintering, the type of agglomeration and/or the type of micro- or nanoparticle. Thus, k describes a "particle class" or "particle type" such as "agglomerates", "aggregates" or "spheres". k may not necessarily be linked to a particle shape, since, e.g., aggregates could have a similar shape like agglomerates. A different classification, for example classification with more classes than the three morphological classes shown in the partial pictures 310 to 314, is also possible. A comparison of the shapes of the agglomerates or particles 318 illustrated in the partial pictures 310 to 314 shows that the shape of the particles 318, which, at sintering temperatures of 20° C. (partial picture 310) over 200° C. (partial picture 312) up to 600° C. (partial picture 314), changes from a loose link (for example morphological class 1, partial picture 310) over a partial sintering (for example morphological class 2, partial picture 312) to a nearly spherical shape (for example morphological class 3, partial picture 314), has a clear influence on the signal of the charge meter 132. This is connected to the fact that the surface area, as can be seen from pictures 310 to 314) decreases with rising sintering temperature and finally approaches the value of a single sphere. As described above, the charge which a particle 318 can assume is strongly connected to the surface area of the particle 318, since more charges can be accepted as the surface area increases.

This connection can be utilized for forming calibration curves, for example, by means of which the primary particle size a and/or other morphological parameters can be inferred from the mobility $d_m$, the charge Q or the current I, and the particle number N. Examples of such calibration curves are illustrated in FIG. 3B. There, the sensitivity S, in this case the current, which was measured by the charge meter 132 (for example the NSAM), is divided by the particle number, which was measured by the counter 130 (for example the CPC) and plotted in the units S (fA cm$^3$) as a function of the mobility diameter $d_m$ in nm. The unit of the sensitivity is the result of the current being usually measured in A or fA per particle, while the particle number can, for example, be given in particles per cm$^3$.

Here, measurement values for three differently sintered particles are plotted, resulting in three different calibration curves 320, 322 and 324. These calibration curves correspond to the sintering temperatures 20° C. 200° C. and 600° C. of the particles 318 according to the partial pictures 310 to 314 in FIG. 3A. Here, a theoretical measurement curve was fitted to the measurement values, which also enables reading of the values in-between and which can form the actual calibration functions 320 to 324, for example.

In principle, a more or less arbitrary theoretical, semi-empirical or empirical curve may be used and may be fitted to the measurement values, as long as the fit allows for deducing the desired one or more morphological parameters, such as the primary particle size and/or the shape factor. As an example to which the scope of the invention is not meant to be restricted, the following theoretical or semi-empirical curve may be used, which will be described in detail. The invention is not bound to the correctness of the theory outlined in the following, and other curves and/or models may be used.

The experimental results lead to the relation between the sensitivity S and the diameter d of a sphere, which, for the case of a simple sphere, corresponds to the mobility $d_m$ in FIG. 3B:

$$S = x(d)^h. \quad (2)$$

It may be assumed that correlation (2) is true for an individual, isolated primary particle with the radius a (here and in the following referred to as the primary particle size):

$$S^P = x(2a)^h. \quad (3)$$

As an example, a loose agglomerate considered, such as the particles 318 in partial picture 310 in FIG. 3A. Physically, the agglomerate is composed of a number of $N_p$ primary particles 316. These primary particles 316, however, generally do not contribute charges as isolated spheres do. Therefore the sensitivity S of the agglomerate is less than $N_p*S^P$. It is assumed that the sensitivity of a loose agglomerate is equivalent to the total sensitivity of $N_c$ isolated primary particles 316, with $N_c < N_p$:

$$S = N_c S^P. \quad (4)$$

Here $N_c$ is an equivalent number of primary particles 316 in the agglomerate particle 318 which indicates the electrical property of the agglomerate.

In theory, it may be assumed that the relation between $N_c$ and $N_p$ can be written as $$N_c = c \cdot N_p^k. \quad (5)$$

Therein, c denotes a factor with 0<c<1. The number of primary particles 316 $N_p$ can be computed using a the following model by Lall and Friedlander:

$$N_p = \frac{3\pi\lambda}{c*a^2} \frac{d_m}{C_c(d_m)}. \quad (6)$$

The meaning of the parameter λ will be discussed in more detail below. Combining the above-mentioned equations (3) to (6), the sensitivity S of a loose agglomerate can be written as $$S = c\left(\frac{3\pi\lambda}{c*a^2}\frac{d_m}{C_c}\right)^k \times (2a)^h \quad (7)$$

$$= c\left(\frac{3\pi\lambda}{c*}\right)^k \left(\frac{d_m}{C_c}\right)^k \times 2^h a^{h-2k}$$

$$= A\left(\frac{d_m}{C_c}\right)^k a^{h-2k}$$

where $A = c\left(\frac{3\pi\lambda}{c*}\right)^k \times 2^h$.

The parameters in the fitting correlation (7) are discussed as follows. λ is the mean free path of the gas molecules. c* is a parameter known from a theoretical model used by Dahneke and Lall & Friedlander. When the aggregate orientation is random, the value of c* is 9.34 for diffuse reflection and 6.85 for specular reflection. The value of c* changes for different orientations. In the fitting procedure, c* is a constant once the orientation is decided. x and h are parameters taken from experimental data and from correlation (2). The two parameters which may be adjusted are c and k. Therein, k denotes a shape factor, which characterizes the morphology of the particles 316, such as the three different morphological classes shown in the partial pictures 310, 312 and 314 and as discussed above.

In this theoretical or semi-empirical approach, the goal of the fitting may be to determine the primary particle size a.

Experimental data of loose agglomerates typically may provide the sensitivity S as a function of $d_m$, as e.g. shown in FIG. 3B. A fitting procedure can be described as follows. Assuming the values of both c and k are known, then a is known, and correlation (7) can be written as $$S^{\frac{1}{h-2k}} = A^{\frac{1}{h-2k}} \left(\frac{d_m}{C_c}\right)^{\frac{k}{h-2k}} a. \quad (8)$$

Now a linear fitting can be done between $$S^{\frac{1}{h-2k}} \text{ and } A^{\frac{1}{h-2k}} \left(\frac{d_m}{C_c}\right)^{\frac{k}{h-2k}}.$$

Then the slope of the linear correlation is a.

The values of c and k need to be determined. The logical way is to assign c and k values so that the value of primary size a is close to the physical value obtained from electron micrograph. This way can be considered the optional calibration step of the fitting method, using an offline characterization, such as electron micrography. Additionally or alternatively, literature values and/or databases may be used. Thus, e.g., data for silver and $SiO_2$ agglomerates are available to complete this calibration. The values of c and k for silver and $SiO_2$ and/or other agglomerates may be implemented in the evaluation step, such as by using a software.

For a new type of agglomerates without prior calibration, the values of c and k generally may not be known. From previous experimental data, the values of c and k for different types of loose agglomerates can be different, but they typically may remain in a certain range. In this case, one option is to use the predetermined values of c and k, such as by using default values in the software, for the new and unknown type of agglomerates. The error of such an approach generally is not known but may be acceptable. Another option, which may be used additionally or alternatively, is to allow an operator to change the value of c and k and observe the change of a. With more applications and more experimental data, the database of the fitting parameters c and k can grow and cover more types of agglomerates.

Since each of the calibration curves 320 to 324, whose number can in principle be expanded as desired, characterizes a different primary particle size a, and/or a different shape factor k and/or other morphological parameters, it is now possible, if the mobility $d_m$ (according to the setting of the classifier 124) and the sensitivity S (from the measurement values N and Q or I) is known, to ascertain a specific calibration curve which corresponds to those values. It is possible, for example, for a family of calibration curves to be stored in a data store, wherein a comparison of S and d, with the stored calibration curves can be used to select the appropriate calibration curve. The primary particle size a and/or the shape factor k and/or other morphological parameters associated with this calibration curve may then be the result (if appropriate the temporary result) of the evaluation of the evaluation step.

The method illustrated in FIG. 2A so far merely represents a static method in which the primary particle size a and/or the shape factor k and/or other morphological parameters are determined for a single particle fraction, i.e. a single particle class selected by the classifier 124. In FIG. 2B, this method is expanded by different classes being selected one after the other and the primary particle size a being determined accordingly. This means that the method variant illustrated in FIG. 2B is a scan method.

In accordance with the method described above in FIG. 2A, for each class the primary particle sizes a are determined. It is possible in this way to determine for example distributions of target variables X derived from the primary particle size a. Examples of this may be number distributions, surface distributions, volume distributions, mass and/or mass distributions or shape factors of agglomerated particles with loose structures.

FIGS. 5 and 6 show that such target variable distributions, which are derived from the primary particle sizes a and describe the actual shape of the agglomerated particles 318 (see the partial pictures 310 to 314 in FIG. 3A) better than the mobility diameter $d_m$, which assumes an idealizing sphere shape, can lead to significant deviations from conventional measurement methods. For example, the surface distribution of an aerosol (again sintered silver particles were used here as a model system) is plotted for example in FIG. 5 as an example of a target variable X or target variable distribution. The differential surface area fraction dA, divided by the logarithmic class width dlog dp of the particle size, is in each case illustrated. The curve 510 here represents a distribution whose measurement is based on the assumption of a sphere. The curve 512, on the other hand, represents a distribution measurement result in which the above-described method is used to determine the actual primary particle size a and the surface area was inferred from said primary particle size a. It can be seen clearly that the distribution 512 in particular in the range of the maximum significantly exceeds the distribution 510 which was determined in a conventional manner. Since, as illustrated above, the surface area can, however, have a critical influence on for example the toxicological properties of agglomerates, this difference can have a significant effect for example on the toxicological assessment and categorization of the totality of the particles. The same applies, for example, also to other properties of the particle totality connected to the surface area, such as the chemical reactivity, environmental pollution, the process properties or the like. The more realistic assessment of the particle totality thus offers significant advantages in many areas of natural science, technology and medicine.

Analogously to FIG. 5, the volume distribution is plotted as further possible target variable distribution in FIG. 6. Again silver particles were used, which were sintered at room temperature and have a primary particle diameter a of 6.9 nm. Here, the volume distribution of the particles, given in differential volume fraction dV, divided by the logarithmic class width dlog dp of the particle size, is plotted. Here, analogously to curve 510, the curve 610 refers to a distribution which is based on the assumption of a sphere, whereas the curve 612 characterizes a distribution based on an agglomerate with the primary particle diameter a.

In this case, the difference between the more realistic model and the simplified assumption of a sphere, has an even stronger effect than in the case of the surface distribution according to FIG. 5, since in the case of a volume distribution the error generated by the sphere simplification enters the distribution to the power of three. It can be seen clearly that the distribution 612 based on the assumption of an agglomerate lies underneath the distribution 610 based on the sphere assumption. This can be explained illustratively with respect to the partial pictures 310 to 314 in FIG. 3A by the fact that, at identical mass, loose agglomerates have a significantly lower mobility or, as illustrated in the partial pictures, at the same mobility, a lower mass. Even the advance in a more realistic determination of the mass distribution can have significant effects on the prediction of particle properties or of properties of a totality of particles.

Figure 2B:
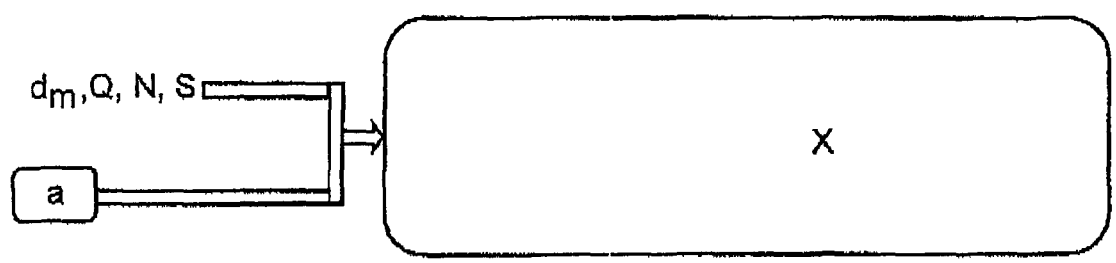

In the method illustrated in FIGS. 2A and 2B first the morphological parameter (for example the morphological class or, by way of example as in the present case, the primary particle size a) is determined statically for a specific particle class, i.e. a particle fraction with prespecified mobility $d_m$, for example using the calibration curves 320 to 324 in FIG. 3B or using another known connection. Subsequently, the scan illustrated in FIG. 2B is carried out. This does not necessarily have to be the case, though. It is also possible, for example, for a scan to be carried out first, in which the charge Q (or the current), the number N and, optionally, therefrom the sensitivity S are determined for a large number of mobilities $d_m$. It is subsequently possible by fitting a fit function to a plot of the variables Q, N and S as a function of the mobility $d_m$ to determine the morphological parameter. One example of such a method variant is illustrated in FIG. 4B. Similarly to FIG. 3B, here the sensitivity S is again plotted as a function of the mobility $d_m$. The measurement points here represent the measurement values ascertained during the scan. A fit function 410 was fitted to these measurement values, which fit function 410 parameterizes with the primary particle size a. The fit functions can, for example, have a linear dependency of the sensitivity S on the mobility $d_m$, an exponential or quadratic connection or another empirically, semi-empirically or theoretically ascertained connection which is fitted to the measurement results in order to determine the primary particle size a. It is thus possible to calculate likewise, as a result of a scan, the primary particle size a from said fit function 410. In the present case, for example, the primary particle size was determined at 6.88 nm.

Figure 4A:
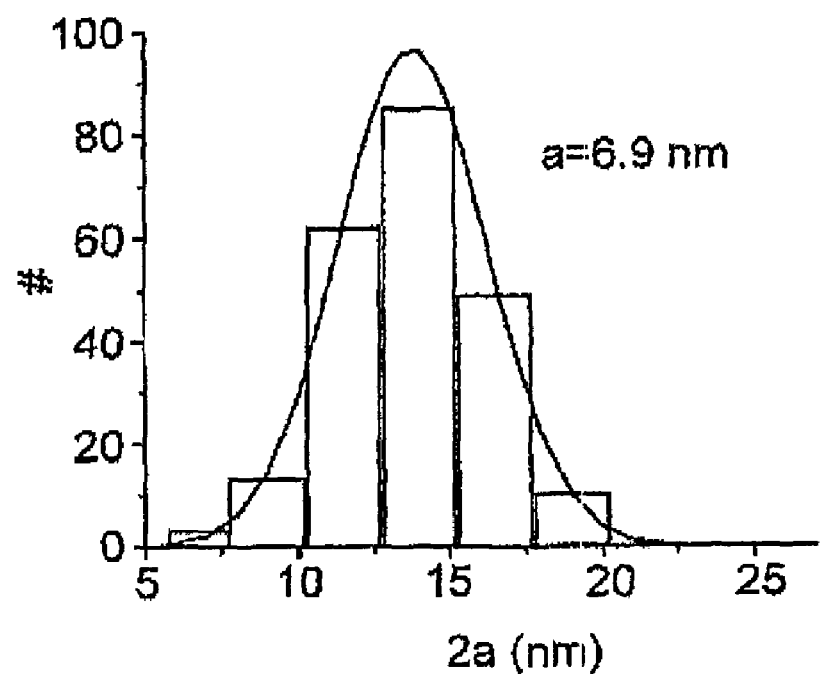
FIG. 4A shows an example of an off-line measurement of a primary particle diameter.
Figure 4B:
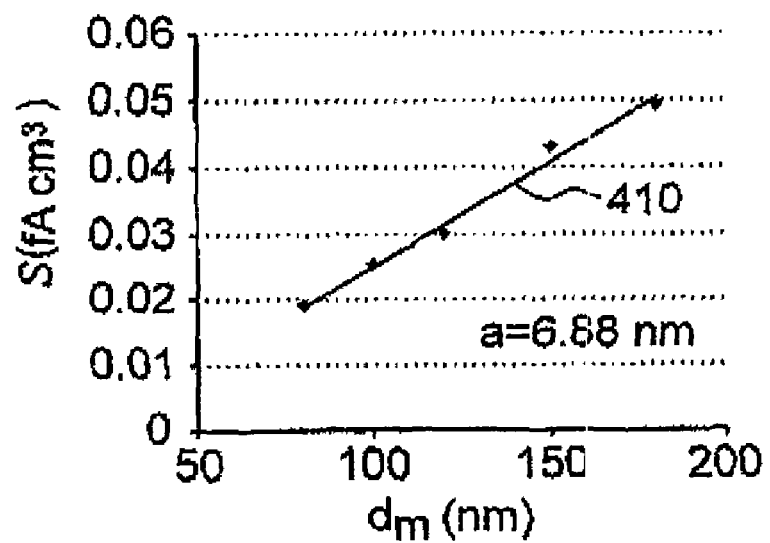
FIG. 4B shows an example of a determination of the primary particle diameter using a fitting method according to the invention.

In FIG. 4A, a result of a primary particle size determination using an off-line method is illustrated for comparison. This off-line method can comprise, for example, a computer-supported evaluation of results obtained using imaging methods, for example analogously to the partial pictures 310 to 314 in FIG. 3A. Here, in each case the number of optically counted primary particles of a specific size is plotted as a function of the primary particle diameter 2a. An evaluation of 223 points resulted here in a mean value of 6.9 nm, which corresponds well with the value of 6.88 nm ascertained by means of fitting a fit function according to FIG. 4B. This method can thus also be utilized well for determining the primary particle size and target variables optionally derived therefrom.

LIST OF REFERENCES

110 device for characterizing a totality of particles
112 line system
114 aerosol inlet
116 pump
118 mass flow controller
120 controller
122 charge state generator
124 classifier
126 partial line
128 sampler
130 counter
132 charge measuring system
134 first branch
136 second branch
138 bypass line
210 classification step
212 counting step
214 charge determination step
216 detection of the sensitivity
218 evaluation step
310 image agglomerate with sintering temperature 20° C.
312 image agglomerate with sintering temperature 200° C.
314 image agglomerate with sintering temperature 600° C.
316 primary particles
318 particles
320 calibration curve for sintering temperature 20° C.
322 calibration curve for sintering temperature 200° C.
324 calibration curve for sintering temperature 600° C.
410 fit function
510 distribution based on sphere
512 distribution based on agglomerate
610 distribution based on sphere
612 distribution based on agglomerate

We claim:

1. A method for characterizing a totality of particles, comprising the following steps:
    a) in a classification step using a classifier, a class of the totality is selected, wherein the particles of the selected class have a prespecified mobility $d_m$;
    b) in a counting step using a counter, a number N of the particles of the selected class is determined;
    c) in a charge determination step using a charge meter, a charge Q of the particles of the selected class is determined; and
    d) in an evaluation step using a calibrator, at least one morphological parameter is determined from the charge Q, the number N and the mobility $d_m$, wherein the morphological parameter comprises at least one item of information about an agglomerate state of the particles,
    wherein a line system is used for guiding a flow of the particles, wherein the classifier, the counter and the charge meter are connected to the line system, and wherein the counter and the charge meter are arranged in parallel branches of the line system.

2. The method according to claim 1, wherein the totality of particles comprises an aerosol.

3. The method according to claim 1, wherein the particles are selected from the group consisting of microparticles and nanoparticles.

4. The method according to claim 1, wherein the at least one morphological parameter comprises at least one of the following items of information: information about a categorization into morphological agglomeration classes; internal porosity and/or an agglomerate or aggregate porosity; apparent density, an agglomerate or aggregate density; a number of primary particles per particle; a primary particle size a; a primary particle size distribution; a shape factor.

5. The method according to claim 4, wherein the item of information is information about a distinction between loose agglomerates, partially aggregated particles and aggregates.

6. The method according to claim 1, wherein, in a scanning step, said method steps are carried out repeatedly individually, in groups or overall, wherein a different class of the totality is selected with each repetition.

7. The method according to claim 6, wherein the steps a) to c) are carried out repeatedly individually, in groups or overall.

8. The method according to claim 1, wherein, in the evaluation step, a known relationship between the charge Q, the number N and the mobility $d_m$, and the morphological parameter is used.

9. The method according to claim 8, wherein the known relationship comprises at least one of a calibration function and a calibration curve, determined by one of the following means: empirical means, semi-empirical means, analytical means.

10. The method according to claim 8, wherein the known relationship is determined by the use of a plurality of test particles, wherein the morphological parameter of the test particles is determined by an imaging method and wherein the variables Q, N and $d_m$ of the test particles are determined by a method comprising
    a) in a classification step, a class of the totality is selected, wherein the particles of the selected class have a prespecified mobility $d_m$;
    b) in a counting step, a number N of the particles of the selected class is determined;
    c) in a charge determination step, a charge Q of the particles of the selected class is determined.

11. The method according to claim 1, wherein a sensitivity S is formed from the charge Q and the number N, wherein the sensitivity S is a function of the charge Q and the number N.

12. The method according to claim 11, wherein the sensitivity S comprises a quotient of the charge Q and the number N.

13. The method according to claim 1, wherein the charge Q and the number N are determined for a plurality of different classes with different mobility $d_m$, wherein in the evaluation step for determining the morphological parameter, a fit function, which is parameterized with the morphological parameter, is fitted to the charge Q and the number N and/or a sensitivity S formed from the charge Q and the number N, wherein the sensitivity S is a function of the charge Q and the number N.

14. The method according to claim 1, wherein, in an evaluation step using the morphological parameter, at least one target variable X, which is different from the variables $d_m$, Q and N, is determined, wherein the target variable X at least partially characterizes the selected class of the particles.

15. The method according to claim 14, wherein the target variable X comprises at least one of the following target variables: a number of the particles; a surface area of the particles; a volume of the particles; a mass of the particles; a shape factor of the particles; a number of primary particles per agglomerate; a surface distribution; a volume distribution; a mass distribution; a shape factor distribution; a number distribution; an internal porosity and/or an agglomerate or aggregate porosity; an apparent density; an agglomerate or aggregate density.

16. The method according to claim 15, wherein at least the method steps a) to c) are repeated with different classes with different mobility $d_m$, wherein in each case the target variable X is ascertained, wherein a target variable distribution, is ascertained.

17. The method according to claim 16, wherein the target variable distribution is a target variable distribution as a function of the mobility $d_m$.

18. The method according to claim 1, wherein in at least one charge generation step, a defined charge state of the particles and/or of the selected class is established.

19. The method according to claim 18, wherein the charge generation step is carried out before or during at least one of method steps a) and method steps c).

20. The method according to claim 1, wherein in a sampling step, a quantity of the particles of a selected class is removed, wherein the quantity of the particles removed are introduced into an alternative characterization method.

21. The method according to claim 20, wherein the alternative characterization method is an imaging method.

22. A device for characterizing a totality of particles, wherein the device comprises the following elements:
   a) a classifier which is designed for selecting a class of the totality, wherein the particles of the selected class have a prespecified mobility $d_m$;
   b) a counter which is designed for determining a number N of the particles of the selected class;
   c) a charge meter which is designed for determining a charge Q of the particles of the selected class; and
   d) a calibrator which is designed for determining at least one morphological parameter from the charge Q, the number N and the mobility $d_m$, wherein the morphological parameter comprises at least one item of information about an agglomerate state of the particles,
   wherein the device comprises a line system for guiding a flow of the particles, wherein the classifier, the counter and the charge meter are connected to the line system, and wherein the counter and the charge meter are arranged in parallel branches of the line system.

23. The device according to claim 22, wherein the totality of particles comprises an aerosol.

24. The device according to claim 22, wherein the particles are selected from the group consisting of microparticles and nanoparticles.

25. The device according to claim 22, wherein the device is designed for carrying out a method comprising the following steps:
   a) in a classification step, a class of the totality is selected, wherein the particles of the selected class have a prespecified mobility $d_m$;
   b) in a counting step, a number N of the particles of the selected class is determined;
   c) in a charge determination step, a charge Q of the particles of the selected class is determined; and
   d) in an evaluation step, at least one morphological parameter is determined from the charge Q the number N and the mobility $d_m$, wherein the morphological parameter comprises at least one item of information about an agglomerate state of the particles.

26. The device according to claim 25, comprising a controller, wherein the controller comprises at least one data-processing machine.

27. The device according to claim 22, wherein the flow of the particles comprises a volume flow and/or a mass flow.

28. The device according to claim 22, wherein a branching ratio between a first partial flow rate through a first branch to which the counter is connected and a second partial flow rate through a second branch to which the charge meter is connected is known or can be set.

29. The device according to claim 28, wherein the first and the second partial flow rates are equivalent.

30. The device according to claim 22, furthermore comprising at least one bypass line, wherein the bypass line is designed for guiding a bypass flow past the counter and/or the charge meter.

31. The device according to claim 22, furthermore comprising at least one sampler, wherein the sampler is designed for removing a quantity of the particles of a selected class and introducing them to an alternative characterization method.

32. The device according to claim 31, wherein the alternative characterization method is selected from the following: an off-line characterization method; an imaging method; a chemical analysis.

33. The device according to claim 31, wherein the sampler is connected to the line system.

34. The device according to claim 22, wherein the classifier has at least one of the following devices: an electrostatic classifier; a diffusion classifier; an impaction classifier; a particle mass spectrometer.

35. The device according to claim 34, wherein the classifier is an electrostatic classifier, which is a differential mobility analyzer.

36. The device according to claim 22, wherein the counter has at least one of the following devices: a condensation particle counter; a condensation nucleus counter; a laser counter; an electrostatic counter which is designed for inferring a particle number from an electric current caused by charged particles; an electrostatic counter which is designed for inferring a particle flow rate from an electric current caused by charged particles.

37. The device according to claim 22, wherein the charge meter comprises at least one of the following devices: a current measurement device for measuring an electric current caused by charged particles; a Faraday cup electrometer; a particle surface area meter; a nanoparticle surface area monitor.

38. The device according to claim 22, furthermore comprising at least one charge state generator, wherein the charge state generator is designed for imposing a defined charge state on at least one of the particles and the selected class of the particles.

39. The device according to claim 38, wherein the charge state generator is selected from the group consisting of a charge state generator which is connected upstream of the classifier and a charge state generator which is connected downstream of the classifier.

40. The device according to claim 38, wherein the charge state generator comprises at least one of the following devices: a bipolar charger; a neutralizer; a charge state generator which is based on a radioactive radiation source; a charge state generator which is based on an electric field; a charge state generator which is based on a light beam; a charge state generator which is based on UV light; a charge state generator which is based on a corona discharge.

41. A method for aerosol monitoring in one of the fields selected from environmental analysis, occupational safety and toxicology, wherein the device according to claim 22 is used.

42. A method for aerosol monitoring in the field of process control, wherein the device according to claim 22 is used, wherein a method is used which is based on the use of at least one aerosol, wherein the aerosol is monitored by means of the device.

* * * * *